(12) United States Patent
Caro et al.

(10) Patent No.: US 8,226,704 B2
(45) Date of Patent: Jul. 24, 2012

(54) HELICAL STENT

(75) Inventors: Colin G. Caro, London (GB); Nicholas V. Watkins, London (GB); Brian G. Falzon, London (GB); Philip L. Birch, Chiddingfold (GB)

(73) Assignee: Veryan Medical Limited, Chiddingfold (GB)

( * ) Notice: Subject to any disclaimer, the term of this patent is extended or adjusted under 35 U.S.C. 154(b) by 192 days.

(21) Appl. No.: 10/549,355

(22) PCT Filed: Mar. 18, 2004

(86) PCT No.: PCT/GB2004/001155
§ 371 (c)(1),
(2), (4) Date: Jul. 31, 2006

(87) PCT Pub. No.: WO2004/082533
PCT Pub. Date: Sep. 30, 2004

(65) Prior Publication Data
US 2006/0265051 A1    Nov. 23, 2006

(30) Foreign Application Priority Data

Mar. 18, 2003 (GB) .................................. 0306176.9
Jul. 21, 2003 (GB) .................................. 0317003.2

(51) Int. Cl.
*A61F 2/06* (2006.01)
(52) U.S. Cl. ...................... 623/1.17; 623/1.22; 623/1.3
(58) Field of Classification Search .................. 623/1.11, 623/1.1, 1.12–1.2, 1.22, 1.28–1.3, 1.32–1.33, 623/1.42–1.43, 1.46–1.48, 1.53, 1.35; 606/191, 606/192, 194, 198, 1.13
See application file for complete search history.

(56) References Cited

U.S. PATENT DOCUMENTS

| | | | |
|---|---|---|---|
| 4,596,548 A | 6/1986 | DeVries et al. | |
| 5,156,619 A | 10/1992 | Ehrenfeld | |
| 5,295,959 A | 3/1994 | Gurbel et al. | |
| 5,308,356 A | 5/1994 | Blackshear, Jr. et al. | |
| 5,370,691 A * | 12/1994 | Samson ....................... | 623/1.22 |
| 5,383,856 A | 1/1995 | Bersin | |
| 5,484,411 A * | 1/1996 | Inderbitzen et al. ..... | 604/103.08 |
| 5,545,132 A | 8/1996 | Fagan et al. | |
| 5,618,299 A | 4/1997 | Khosravi et al. | |
| 5,649,978 A | 7/1997 | Samson | |

(Continued)

FOREIGN PATENT DOCUMENTS

EP         0 275 230 A2    7/1988

(Continued)

OTHER PUBLICATIONS

Min Invas Ther & Allied Technol 2002: 11(4) pp. 173-178, Entitled: A Comparison of Balloon- and Self-Expanding Stents.

(Continued)

*Primary Examiner* — Kathleen Sonnett
*Assistant Examiner* — Jocelin Tanner
(74) *Attorney, Agent, or Firm* — Fay Sharpe LLP

(57) ABSTRACT

A stent for insertion in a fluid conduit of a human or animal body when the stent is in a collapsed condition and for expansion to an expanded condition, includes an outer wall for engagement with the conduit. The outer wall has a helical portion which in the expanded condition extends longitudinally and circumferentially, and which, upon expansion of the stent from the collapsed condition to the expanded condition, resists extension.

14 Claims, 9 Drawing Sheets

U.S. PATENT DOCUMENTS

| | | | |
|---|---|---|---|
| 5,653,745 A | | 8/1997 | Trescony et al. |
| 5,709,713 A * | | 1/1998 | Evans et al. ............... 623/1.53 |
| 5,733,327 A * | | 3/1998 | Igaki et al. ................. 623/1.5 |
| 5,735,816 A | | 4/1998 | Lieber et al. |
| 5,800,456 A * | | 9/1998 | Maeda et al. ............. 623/1.15 |
| 6,053,943 A * | | 4/2000 | Edwin et al. ............. 623/1.25 |
| 6,364,904 B1 * | | 4/2002 | Smith ....................... 623/1.22 |
| 6,375,660 B1 * | | 4/2002 | Fischell et al. ............. 606/108 |
| 6,425,908 B2 | | 7/2002 | Ravenscroft et al. |
| 6,527,739 B1 | | 3/2003 | Bigus et al. |
| 6,569,191 B1 * | | 5/2003 | Hogan ...................... 623/1.11 |
| 6,596,023 B1 * | | 7/2003 | Nunez et al. ............... 623/1.3 |
| 6,896,007 B2 * | | 5/2005 | Cymbalisty ............... 138/177 |
| 2001/0049549 A1 | | 12/2001 | Boylan et al. |
| 2002/0022877 A1 | | 2/2002 | Mueller et al. |
| 2002/0035390 A1 | | 3/2002 | Schaldach et al. |
| 2002/0049487 A1 | | 4/2002 | Lootz et al. |
| 2002/0116044 A1 | | 8/2002 | Cottone |
| 2002/0179166 A1 * | | 12/2002 | Houston et al. ............. 138/39 |
| 2004/0039443 A1 | | 2/2004 | Solem et al. |
| 2006/0047334 A1 | | 3/2006 | Houston et al. |
| 2006/0124187 A1 | | 6/2006 | Houston et al. |
| 2007/0112407 A1 | | 5/2007 | Mertens et al. |
| 2007/0213663 A1 | | 9/2007 | Wang |

FOREIGN PATENT DOCUMENTS

| | | | |
|---|---|---|---|
| EP | 0 699 423 A2 | | 3/1996 |
| EP | 0 714 640 A1 | | 6/1996 |
| EP | 0 581 900 B1 | | 2/1998 |
| EP | 0 612 536 B1 | | 12/1999 |
| EP | 1 042 997 A1 | | 10/2000 |
| EP | 1 127 557 A1 | | 8/2001 |
| EP | 1254645 A1 | * | 11/2002 |
| EP | 1 269 935 | | 1/2003 |
| EP | 1 279 382 A1 | | 1/2003 |
| EP | 2 292 183 A1 | | 3/2011 |
| FR | 2 248 015 A1 | | 5/1975 |
| FR | 2 657 945 A3 | | 8/1991 |
| FR | 2 666 502 A1 | | 3/1992 |
| GB | 2 092 894 A | | 8/1982 |
| GB | 2 298 577 A | | 9/1996 |
| GB | 2 344 053 A | | 5/2000 |
| GB | 2 425 485 A | | 11/2006 |
| JP | 07-507697 | | 8/1995 |
| JP | 08-257139 | | 10/1996 |
| JP | 2001-252987 A | | 9/2001 |
| WO | WO 95/09585 A1 | | 4/1995 |
| WO | WO 95/17223 A1 | | 6/1995 |
| WO | WO 95/35072 A2 | | 12/1995 |
| WO | WO 97/24081 A1 | | 7/1997 |
| WO | WO 98/26731 A2 | | 6/1998 |
| WO | WO 98/26731 A3 | | 6/1998 |
| WO | WO 98/53764 A2 | | 12/1998 |
| WO | WO 99/17682 | | 4/1999 |
| WO | WO 00/32241 | | 6/2000 |
| WO | WO 00/38591 A | | 7/2000 |
| WO | WO 00/38591 A2 | | 7/2000 |
| WO | WO 00/38591 A3 | | 7/2000 |
| WO | WO 00/49973 | | 8/2000 |
| WO | WO 01/45593 A1 | | 6/2001 |
| WO | WO 01/89420 A2 | | 11/2001 |
| WO | WO 02/066095 A2 | | 8/2002 |
| WO | WO 02/098325 A2 | | 12/2002 |
| WO | WO 03/000157 A1 | | 1/2003 |
| WO | WO 03/045278 A1 | | 6/2003 |
| WO | WO 03/103540 | | 12/2003 |
| WO | WO 2004/047908 | | 6/2004 |
| WO | WO 2004/066852 A2 | | 8/2004 |
| WO | WO 2004/082533 A1 | | 9/2004 |

OTHER PUBLICATIONS

Min Invas Ther & Allied Technol 2002: 11(4) pp. 137-147, Entitled: A Survey of Stent Designs.
Eur. J. Vasc. Endovasc. Surg 24, pp. 13-22 (2002), Entitled: External Supports and the Prevention of Neointima Formation in Vein Grafts.
Partial European Search Report, dated Dec. 21, 2009, 5 pages.
European Search Report of corresponding European Application No. EP 10 01 0780 dated Dec. 9, 2010.

* cited by examiner

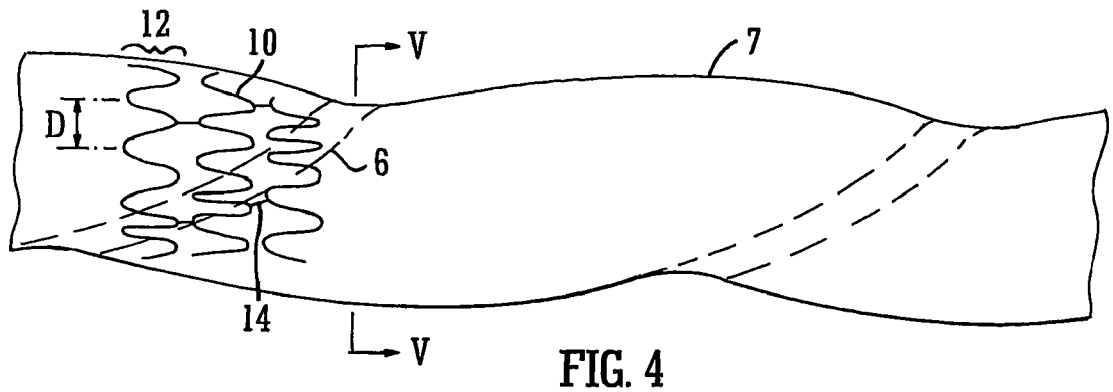
FIG. 4
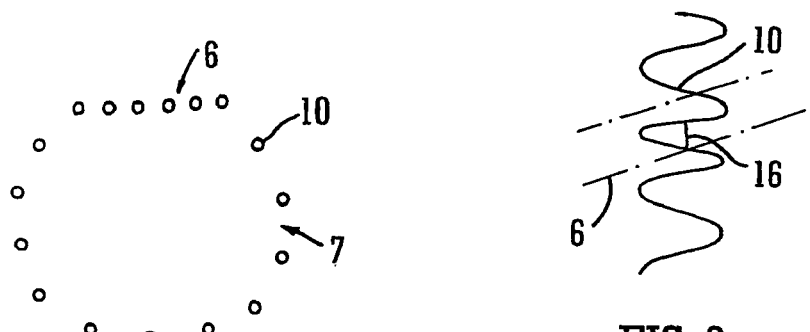
FIG. 5
FIG. 6
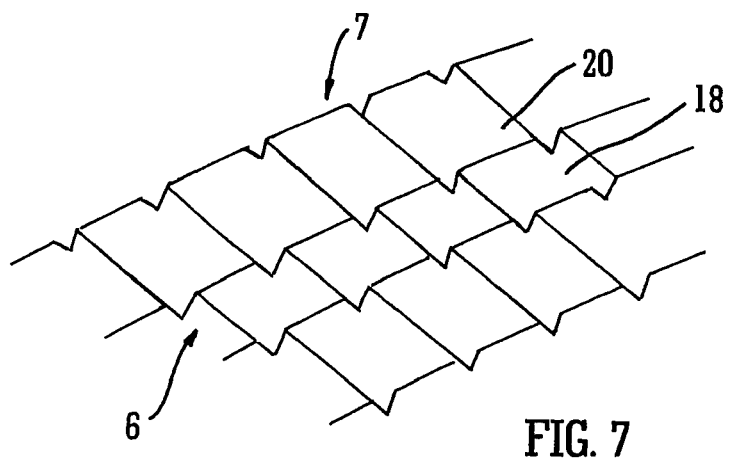
FIG. 7

HELICAL STENT

This invention relates to stents for insertion in a fluid conduit of the human or animal body.

Stents are generally tubular devices used for providing physical support to blood vessels, i.e. they can be used to help prevent kinking or occlusion of blood vessels such as veins or arteries and to prevent their collapse after dilatation or other treatment.

Stents can be broadly divided into two main categories: balloon expandable stents and self-expanding stents. In the case of the former the material of the stent is plastically deformed through the inflation of a balloon, so that after the balloon is deflated the stent remains in the expanded shape. Such stents are manufactured in the "collapsed" condition, ready for delivery, and may be expanded to the expanded condition when inside the vessel or other fluid conduit.

Self-expanding stents are also designed to be delivered in the collapsed condition and when released from a constraining delivery system the stent expands to its expanded condition of a predetermined size. This effect is achieved by using the elasticity of the material and/or a shape-memory effect. In the case of shape-memory stents a commonly used material is nitinol.

Many different designs of stents are available on the market. They are made from a variety of materials providing corrosion resistance and biocompatibility. They are made from sheet, round or flat wire or tubing. They are generally cylindrical but also longitudinally flexible so as to conform to the curvature of the fluid conduit into which they are inserted.

It has been proposed in EP 1042997 to provide stents the flexibility of which varies along their length, in order to facilitate placement of one end of the stent in a narrower or tortuous coronary artery, or to achieve stenting of a bend of a particular coronary artery. This proposal involves providing the stent with a pattern of interconnected struts, with the strut thickness being variable along the length of the stent.

We have previously proposed that the flow pattern in arteries including the swirling pattern induced by their non-planar geometry operates to inhibit the development of vascular diseases such as thrombosis, atherosclerosis and intimal hyperplasia.

In WO 98/53764, there is disclosed a stent for supporting part of a blood vessel. The stent includes a supporting portion around which or within which part of a blood vessel intended for grafting can be placed so that the stent internally or externally supports that part. The supporting portion of the stent is shaped so that flow between graft and host vessel is caused to follow a non-planar curve. This generates a swirl flow, to provide a favourable blood flow velocity pattern which reduces the occurrence of vascular disease, particularly intimal hyperplasia.

In WO 00/32241, there is disclosed another type of stent, in this case including a supporting portion around which or within which part of an intact blood vessel other than a graft can be placed. This supporting portion can prevent failure of the vessel through blockage, kinking or collapse. Again, the supporting portion of the stent is of a shape and/or orientation whereby flow within the vessel is caused to follow a non-planar curve. Favourable blood flow velocity patterns can be achieved through generation therein of swirl flow within and beyond the stent. Failures in blood vessels through diseases such as thrombosis, atherosclerosis, intimal hyperplasia can thereby be significantly reduced.

Further aspects of how swirl flow is beneficial are explained in the above publications. It is further explained in Caro et al. (1998) J. Physiol. 513P,2P how non-planar geometry of tubing inhibits flow instability.

It has been proposed in WO 00/38591 to provide a stent with internal helical grooving or ridging to induce helical flow. FIGS. 9 to 12 of this document show a stent in the form of a mesh cylinder, with vane members attached to the inside of the cylinder so as to project into the fluid passage and guide the flow. However the presence of vanes projecting into the flow may obstruct the flow and increase flow resistance, especially if there is any build-up of material on the vanes. Also, the use of vanes in an otherwise cylindrical tube may not reliably induce swirl flow across the entire cross-section of flow. There may be a tendency for the flow nearer to the centre of the tube to follow a linear path, particularly for flows at higher Reynolds numbers. Further, the provision of vanes over a relatively short length of flow is likely to create only a temporary alteration of flow characteristics, with the flow reverting to a normal pattern at a distance downstream of the vanes.

In WO 02/098325 there are various proposals for cylindrical external structures for placement outside of blood flow conduits in order to influence the internal geometry of the conduit lumen. By providing ribs or other radially inwardly projecting helical members, the cross-sectional shape of the lumen is modified from the outside of the conduit. The various structures are not for use as stents capable of delivery internally of a conduit in a collapsed condition and for expansion at the target site.

In WO 00/32241 internal stents for establishing and/or maintaining non-planar curvature of a blood vessel are shown. FIG. 5 of this document shows a clip which is part coiled or at least part helical of shape memory alloy, affixed to a cylindrical wire mesh. With such an arrangement, when the clip moves to a more coiled condition once the stent has been installed, it will cause the cylindrical wire mesh to adopt a non-planar curvature but it will also cause it to twist. Since it is undesirable for the stent to apply torsional loading to the inside wall of the blood vessel, this twisting effect may limit the number of helical turns imposed by the clip, for example to one or less than one turn. However, the objective of inducing or maintaining swirl flow in the vessel is assisted by increasing the number of helical turns. The clip also forms a rib projecting into the flow lumen of the blood vessel which, as discussed above in relation to vane members, may not be ideal for the flow characteristics of the vessel.

We have now found a way of producing an internal stent capable of moving from a collapsed condition to an expanded condition without significant twisting but which facilitates flow within the stent supported fluid conduit to follow a non-planar curve, i.e. to swirl.

According to a first aspect of the invention there is provided a stent for insertion in a fluid conduit of the human or animal body when the stent is in a collapsed condition and for expansion to an expanded condition, the stent comprising an outer wall for engagement with the conduit, the outer wall having a helical portion which in the expanded condition extends longitudinally and circumferentially, and which, upon expansion of the stent from the collapsed condition to the expanded condition resists extension.

Flow within the fluid conduit supported by such a stent can follow a non-planar curve, promoting swirl flow, the benefits of which are discussed above. Thus, considering the flow lumen of the conduit, as this extends in the longitudinal direction x-axis) it curves in more than one plane (i.e. in both the y-axis and the z-axis). In other words, the flow lumen extends generally helically in the longitudinal direction. Such a non-planar curve may be achieved by a non-rotationally symmetric shape (rotational symmetry of order one) when in the expanded condition, which "twists" along the length of the stent. It may however also be achieved if the stent has a circular or other rotationally symmetrical cross-sectional shape, providing the cross-section as a whole shifts laterally from one "slice" to the next. In some instances, a combination of a non-rotationally symmetric shape which twists and which shifts laterally is provided.

Preferably, when the stent is in its expanded condition, it causes the fluid conduit to follow a non-planar curve as it extends in the longitudinal direction and the curve undergoes at least one turn. The provision of more than one turn, more preferably a plurality of turns, is enabled by the ability of preferred stents to expand from the collapsed condition to the expanded condition without substantial twisting, i.e. there is no significant rotation of one end of the stent relative to the other. This can be achieved by the helical portion having the same number of turns both when the stent is collapsed and when it is expanded. This property of the stent means that it can expand without causing the conduit to twist, which would be undesirable because of the tethering of the conduit in the human or animal body.

Preferably, the centre line of the stent in the expanded condition follows a substantially helical path. In other words, the centroids of adjacent cross-sectional slices through the stent define a helical locus or centre line.

It is generally preferred to avoid any pronounced grooves, ridges, ribs or vanes, as these may have the opposite of the desired effect of improving flow characteristics, i.e. they may obstruct the flow, facilitate deposit build up or create stagnant regions. Preferably, therefore, the stent is substantially free of ribs or vanes, for example free of thicker wires (than adjacent wires) which would act as a rib projecting into the flow lumen of the flexible conduit.

The stent improves flow characteristics. As is well known, in the case of straight tubes, near wall velocities are very low compared to velocities at the core of the tube, due to the effects of viscosity. In the case of tubes which are bent in a single plane, the speed of the flow at the outside of the bend is increased but the speed of the flow at the inside is retarded further. In both cases, there is considerable variation in axial velocity across the width of the tube. With the use of a helical tubing portion according to the invention, a swirl flow is generated and the axial velocity profile of the flow across the tubing portion becomes generally more uniform or "blunter", with the axial velocity of flow at both the outside and inside of the tubing portion being closer to the mean axial velocity.

Thus, the flow characteristics are improved by causing swirling and a relatively uniform distribution of axial and near wall velocity. Mixing over the cross section is also promoted and there is a reduction in the likelihood of occurrence of flow instability. The avoidance and flushing of stagnant zones is assisted. There is a reduction in the potential for deposit build up within and downstream of the graft and the development of pathology.

The amplitude and pitch of the helical centre line may be chosen to vary along the length of the stent, if desired. Variation of amplitude can be achieved by increasing or decreasing the resistance to extension provided by the helical portion, whilst variation in pitch may be achieved by varying the pitch of the helical portion itself. Such variations may for example be desired if it is wished to introduce a gentle swirl at the upstream end of the stent and to increase the swirl effect in the downstream direction.

The stents of the preferred embodiments have a helical portion which has a greater resistance to extension than portions of the stent adjacent to the helical portion. Preferably, the helical portion comprises an increased amount of stent forming material relative to the amount of stent forming material in portions of the stent adjacent to the helical portion. The increased amount of material can provide the required resistance to extension when the stent expands to the expanded condition. The increase may be provided for example by thicker structural members, in the radial direction and/or longitudinal direction and/or circumferential direction. The increased amount may alternatively or additionally be provided by the use of extra stent forming members. For example, in the case of a woven stent, the helical portion may be provided by weaving in one or more extra wires. In other cases, extra struts may be provided.

The helical portion may comprise structural members having bent portions which resist unbending during expansion of the stent. Many stents consist of structural members bent between nodes or at nodes. In general, when the stent expands some or all of the bent portions unbend as the diameter of the stent increases. The desired resistance to extension may therefore be achieved by the helical portion having structural members with bent portions which resist unbending more than bent portions adjacent to the helical portion.

The helical portion may be arranged to resist extension in the circumferential direction, or to resist extension in the longitudinal direction, or to resist extension in the circumferential and the longitudinal directions. The choice of the appropriate form of the helical portion will generally depend on the type of stent and the manner in which it expands.

The helical portion may be viewed as a helical stripe extending longitudinally and circumferentially of the stent. The stripe may be substantially continuous, as for example in the case of one or more extra wires woven into the stent, or it may be discontinuous, as will be the case where the stent has thicker or otherwise modified structural members which are separated by spaces.

The stent may be of the self-expanding type or it may be balloon expandable. In the case of self-expanding stents, during expansion from the collapsed condition to the expanded condition, the portions which are not part of the helical portion will be seeking to expand due to their elasticity or shape-memory properties. The expansion is resisted in the vicinity of the helical portion by being less expansible. The helical portion may itself extend to some degree during expansion of the stent, and indeed may itself be seeking to expand due to its elasticity or shape-memory properties. However, the rest of the stent will be seeking to expand more than the helical portion so that in effect the helical portion provides a resistance to extension. This will enable the stent to assume the desired shape for promoting swirl flow in a fluid conduit supported by the stent.

In the case of a balloon expandable stent, the force to expand the stent is supplied by the balloon and the helical portion will allow less expansion, which will normally mean a lesser degree of plastic deformation, than the rest of the stent.

The basic geometry of the stent may be of the many available types, such as coil stents, helical spiral stents, woven stents, sequential ring stents, closed cell sequential ring stents, and open cell stents. They may be made by coiling, braiding or knitting wires, by laser cutting from tubing, by electric discharge milling (EDM), by chemical etching or by other known methods. They may be made from a variety of materials, including stainless steel, nitinol, tantalum, platinum iridium, niobium alloy, cobalt alloy or polymers (such as biodegradable polymers).

According to a second aspect of the invention there is provided a balloon expandable stent for insertion in a fluid conduit of the human or animal body when the stent is in a collapsed condition and for expansion to an expanded condition, the stent comprising a balloon having an expandable wall, the wall having a helical portion which in the expanded condition extends longitudinally and circumferentially, and which, upon expansion of the balloon from the collapsed condition to the expanded condition, resists extension.

In some circumstances the main stent body, i.e. that which is left in the fluid conduit after the balloon is removed, may be of a conventional type before expansion. After expansion, however, it retains (by plastic deformation) a shape which corresponds to that determined by the balloon with the helical portion of reduced extensibility.

Alternatively, the stent may have an outer wall for engagement with the fluid conduit in accordance with the first aspect of the invention, i.e. also with a helical portion which resists extension. The helical portions of the balloon and the stent outer wall would then preferably be arranged in registration with each other.

The helical portion of the balloon expandable wall may have a wall thickness greater than that of adjacent wall portions. This could easily be achieved by adding a helical "stripe" around the outside of a balloon of uniform wall thickness, thereby creating the thicker helical portion.

In certain aspects, the invention is concerned with stents for insertion in flexible conduits of the human or animal body, in which a helical centre line of the flow lumen of the conduit is of relatively small amplitude.

A further proposal in WO 00/38591 is to provide a circular-section tube bent into a cork screw shape. It is usual for the helix of a cork screw to have a clear gap down the middle, so that this proposed configuration would have a wide swept width compared to the width of the tubing, certainly more than two tubing diameters. The amplitude of the helix would be greater than one half of the internal diameter of the tubing and there would be no "line of sight" along the inside of the tubing. This proposal would therefore be relatively bulky and unsuitable for certain applications. A similar proposal is shown in FIG. 5 of WO 02/98325, relating to a tubular mesh structure to be located externally of a conduit, the tubing having a helix with a large amplitude and again no "line of sight" along the inside of the tubing.

According to a third aspect of the invention, there is provided a stent for insertion in a fluid conduit of the human or animal body when the stent is in a collapsed condition and for expansion to an expanded condition, wherein in the expanded condition the stent causes the fluid conduit to have a flow lumen having a centre line which follows a substantially helical path, the helical centre line having a helix angle less than or equal to 65° and an amplitude less than or equal to one half of the internal diameter of the flow lumen.

The features of the third aspect above, and its preferred features below, may also be useful in conjunction with the stents in accordance with the first or second aspects of the invention, individually or in combinations.

The invention is applicable to stents internal to intact blood vessels or blood vessels intended for grafting.

In this specification, the amplitude of the helix refers to the extent of displacement from a mean position to a lateral extreme. So, in the case of the flow lumen having a helical centre line, the amplitude is one half of the full lateral width of the helical centre line.

In the flow lumen, in which the amplitude of the helix is less than or equal to one half of the internal diameter of the tubing, there is a "line of sight" along the lumen of the tubing, unlike in the case of a corkscrew configuration where in effect the helix is wound around a core (either solid, or "virtual" with a core of air). We have found that the flow at the line of sight generally has a swirl component, even though it could potentially follow a straight path.

For the purposes of this specification, the term "relative amplitude" of a helical flow lumen is regarded as the amplitude divided by the internal diameter. So, in the flow lumen in which the amplitude of the helical tubing is less than or equal to one half of the internal diameter of the tubing, this means that the relative amplitude is less than or equal to 0.5. Relative amplitudes less than or equal to 0.45, 0.4, 0.35, 0.3, 0.25, 0.2, 0.15 or 0.1 may be preferred in some circumstances. It is however preferred for the relative amplitude to be at least 0.05, more preferably 0.1. This can help to ensure that the desired swirl flow is induced.

The relative amplitude may vary according to the use of the stent and the spatial constraints on its design. It will however be appreciated that by keeping the amplitude less than half the tubing internal diameter a swirling flow may be induced without creating an excessively large device. The "envelope" occupied by the stented conduit can fit into the space available in the tissue surrounding the fluid conduit, and even if this envelope is caused to follow a particular path by the local environment in which the conduit is located, the desired helical geometry of the flow lumen can be maintained.

It is expected that the conduit may prevent the stent from expanding to its full size. Therefore, the stent may be designed to have a relative amplitude greater than 0.5 (e.g. 0.6 or 0.7), but so that in use a relative amplitude of the flow lumen is equal to or less than 0.5. In certain preferred arrangements, however, the relative amplitude of the expanded stent ex vivo is less than or equal to 0.5.

The angle of the helix is also a relevant factor in balancing the space constraints on the flow tubing with the desirability of maximising the cross-sectional area available for flow. The helix angle is less than or equal to 65°, preferably less than or equal to 55°, 45°, 35°, 25°, 20°, 15°, 10° or 5°. As with relative amplitudes, the helix angle may be optimized according to the conditions: viscosity, density and velocity of fluid.

Generally speaking, for higher Reynolds numbers the helix angle may be smaller whilst satisfactory swirl flow is achieved, whilst with lower Reynolds numbers a higher helix angle will be required to produce satisfactory swirl. The use of higher helix angles will generally be undesirable, as there may be near wall pockets of stagnant fluid. Therefore, for a given Reynolds number (or range of Reynolds numbers), the helix angle will preferably be chosen to be as low as possible to produce satisfactory swirl. Lower helix angles result in smaller increases in length as compared to that of the equivalent cylindrical tubing. In certain embodiments, the helix angle is less than 20° or less than 15°.

It will be appreciated that in pulsatile flow, the Reynolds number will vary over a range. Typical mean resting arterial blood flow Reynolds numbers are about 100, reaching peak values of two or three times that in pulsatile flow and three to four times the mean during exertion. Therefore the extent to which swirl flow is promoted will vary likewise. Even if there are stagnant flow regions at lower Reynolds numbers, because for example a low helix angle and/or a low relative amplitude has been selected, these will tend to be flushed out during periods of flow when the Reynolds numbers are higher.

The stent may be made with substantially the same relative amplitude and helix angle along its length. There may be small variations when the stent is in use, caused by elongation or contraction of the tubing portion due to tensile loading or caused by torsional loading. However, there may be circumstances in which the stent has a variable helix angle and/or relative amplitude, either to suit the space constraints or to optimise the flow conditions.

For reasons of manufacturing simplicity, it may be preferred for the stent to have a substantially constant cross-sectional area along its length. Again, there may be variations in use caused by loading on the stent.

The helical part of the stent may extend along just part of the overall length of the stent or it may extend over substantially its entire length. For example, a stent may have a part with the geometry of the invention over part of its length or over substantially its entire length.

The stent may undergo a fraction of one complete turn, for example one quarter, one half or three quarters of a turn. Preferably, the stent undergoes at least one turn, more preferably at least a plurality of turns. Repeated turns of the helix along the stent will tend to ensure that the swirl flow is generated and maintained.

The stent may extend generally linearly. In other words, the axis about which the centre line of the stent follows a substantially helical path, may be straight. Alternatively the axis may itself be curved, whereby the envelope occupied by the stented conduit is curved, for example to produce an "arch" shaped conduit. The bend of the arch may be planar or non-planar, but should preferably be such that swirl is maintained and not cancelled by the geometry of the bend. Thus, for example, a stent may be generally "arch" shaped (planar or non-planar), having the geometry in accordance with the third aspect of the invention, i.e. such that the stented conduit follows a substantially helical path with a helix angle less than or equal to 65°, and with an amplitude less than or equal to one half of the internal diameter of the tubing portion.

The stent may if desired comprise a pharmaceutical coating. Such a coating could be provided to provide sustained release of the pharmaceutical over a period of time. So, the stent could provide a pharmaceutical for initial treatment of a disease, and in the longer term the stent gives a therapeutic benefit due to the characteristics which it imparts to the flow.

In the above prior art proposals using multiple grooves or ridges arranged about the tubing circumference, or non-circular sections which are twisted, where the tubing is substantially straight, then the centre line of the tubing is also straight. This is unlike the centre line of the stent of the present invention, in its third aspect, which follows a substantially helical path. Thus, the stent may have a substantially circular cross-section and thus the smallest possible wetted perimeter to cross-sectional area ratio, whilst still having the necessary characteristics to induce swirl flow. Of course, there may be circumstances in which the stent has a non-circular cross-section, for example to assist interfacing or where pressure loss considerations are not significant.

There are proposals in WO 97/24081 and EP 1127557 A1 for tubing to have a single internal rib arranged helically. This results in the tubing having a centre line which follows a helical path, but because the rib is provided in an otherwise cylindrical tube, the amplitude of the helix is very small, generally having a relative amplitude appreciably less than 0.05. The generation of swirl flow, if there is any, is correspondingly limited and unsatisfactory.

Further concerning the prior art proposals using grooves or ridges or ribs, it should be noted that arterial geometry is under normal physiological conditions non-planar (i.e. curved in more than one plane in the nature of a helix) and not grooved or rifled. We have found experimentally that at higher relevant Reynolds numbers, the flow in a helical (non-planar) geometry differs from that in a rifled/grooved geometry, e.g. there is swirling of both near-wall flow and core flow in the former case. The development of swirl flow is more rapid than in the case of rifled/grooved tubing, where swirl flow can take many tubing diameters to develop. Thus, there is the expectation that the introduction of the physiological non-planar geometry (unlike grooved or rifled geometry) will be beneficial in respect of inhibiting the development of pathology.

Because the stent of the third aspect of the invention has a helical centre line, there is spatial reorganisation of vortical structures, which results in motion of the core or cores of the axial flow across the section of the stent, promoting mixing across the cross section. The swirl inhibits the development of stagnation and flow separation regions and stabilises flows.

As mentioned, in the case of the prior art proposals using multiple grooves or ridges or ribs, or twisted tubes of a non-circular cross-section, the centre line is straight, not helical. Whilst this can be expected to stabilise flow at sharp bends, it does not in straight tubes cause spatial reorganisation of vortical structures, resulting in motion of the core or cores of the axial flow across the section of the tube. Thus it does not promote mixing across the cross section to the same extent as tubing according to the invention. Such mixing may be important in maintaining the mass transport and physiological integrity of the blood vessels.

The stent geometry disclosed herein may be used in various biomedical applications e.g. in various arteries (such as in the coronary, carotid and renal arteries), in veins, and in non-cardiovascular applications such as in the gastro-intestinal (e.g. bile or pancreatic ducts), genito-urinary (e.g. ureter or urethra) or the respiratory system (lung airways). Thus, the invention extends to stents for body fluids other than blood. In general, the use of the geometry of the invention can avoid the presence of stagnant regions, and hence be beneficial.

Certain preferred embodiments of the invention will now be described by way of example and with reference to the accompanying drawings, in which:

FIG. 4 is a longitudinal cross-sectional view of a second embodiment of stent;

FIG. 5 is a transverse cross-sectional view of the second embodiment on the line V-V of FIG. 4;

FIG. 6 is a fragmentary longitudinal cross-sectional view of a third embodiment of stent;

FIG. 7 is a fragmentary view of a longitudinal cross-section of a fourth embodiment of stent;

Figure 1:
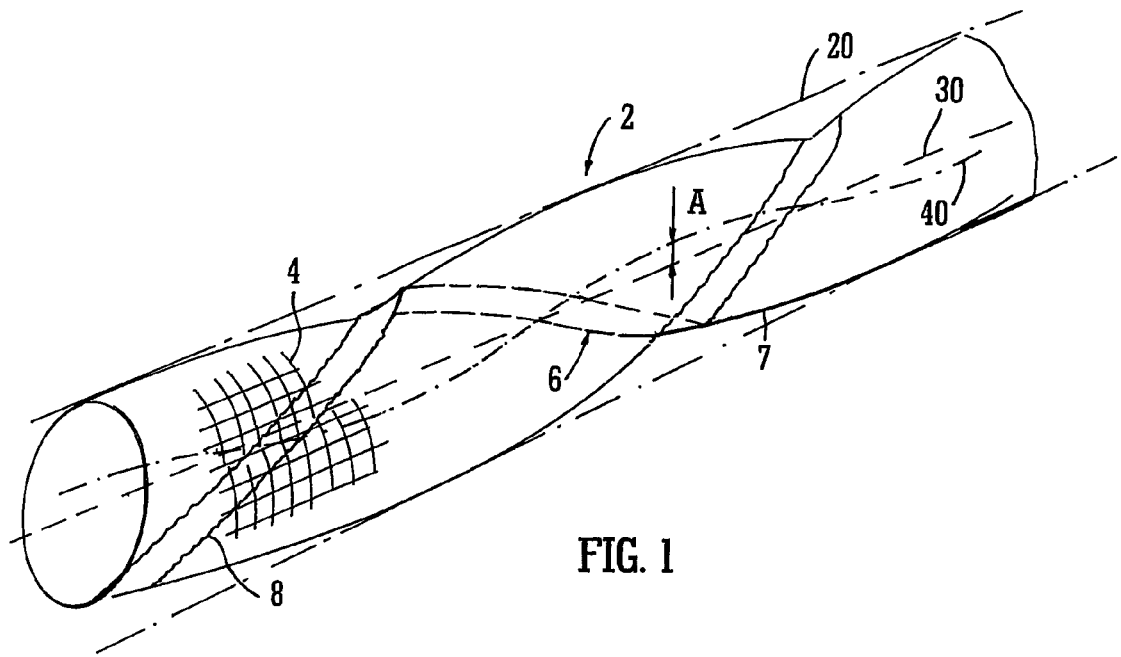
FIG. 1 is a perspective view of a first embodiment of stent in accordance with the invention.
Figure 2:
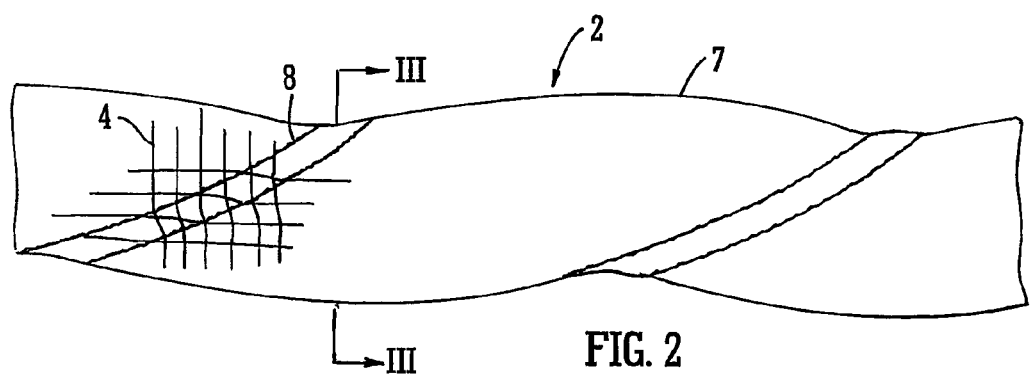
FIG. 2 is a longitudinal cross-sectional of the stent.
Figure 3:
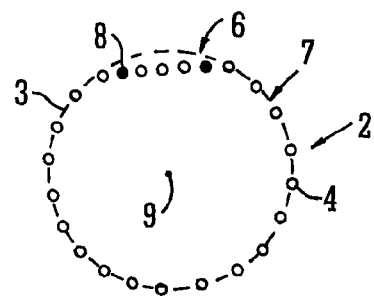
FIG. 3 is a transverse cross-sectional view of the stent on the line III-III of FIG. 2.

FIGS. 1 to 3 show a woven stent 2 in the expanded condition. The stent has the usual wire strands 4 arranged in a mesh and collectively forming a mesh like outer wall 7. It is also provided with a helical portion or "stripe" 6 extending longitudinally and circumferentially of the stent. The helical portion 6 in this case consists of two additional strands 8 woven into the main mesh.

One effect of the helical portion 6 is to create a cross-sectional shape approximating to a circle with a segment removed in the region corresponding to the helical portion, as seen in FIG. 3. This cross-sectional shape has a centroid 9. The locus of centroids 9 along the length of the stent defines a helical centre line 40, shown in FIG. 1. The centre line 40 follows a helical path about a longitudinal axis 30 which is at the centre of an imaginary cylindrical envelope 20 within which the stent is contained. The amplitude A of the helix is shown in FIG. 1.

In practice the amplitude A is greater than would be achieved by merely rotating the cross-sectional shape about the centre of the circle 3. In that case, the envelope 20 would simply correspond to the circle 3. However, the effect of the helical portion resisting extension during expansion is to cause the envelope 20 to be appreciably larger than the circle 3. This is another effect of the helical portion contributing to the creation of a non-planar or helical flow lumen.

In use, the stent is deployed at a target site and is then expanded by a balloon or by the elasticity or shape-memory properties of the strands 4. The helical portion 6 acts to restrict extension (at least in the longitudinal direction) and hence the expanded stent adopts the configuration described, in which the centre line of the stent follows a helical path. The outer wall 7 engages the fluid conduit wall and influences its shape so that the lumen of the fluid conduit at the target site also tends to have a helical centre line. This will help to promote swirl flow along the lumen. The handedness ("s" or "z") of the stent will normally be chosen to complement the local fluid conduit geometry so as to enhance any swirl flow already existing upstream of the stent and not to cancel it.

In the embodiment shown in FIGS. 1 to 3 two helically arranged wires 8 are provided, but other numbers of wires could be used. In addition, the wires could be designed to provide the greatest resistance to extension in the middle of the helical portion 6, with less resistance being provided towards the edges of the helical portion, for example by grading the wires with a thickest wire in the middle and thinner wires towards the edges. Such an arrangement could ensure that the shape of the expanded stent, when viewed in transverse cross-section, does not have any sharp ridges or grooves and ideally corresponds closely to a circle.

In a modified embodiment a helical portion is formed by a single helically arranged wire 8 to produce a stent of substantially circular cross-section. The single wire can provide resistance to longitudinal extension during expansion of the stent and cause it to define a lumen with a helical centre line. A circular cross-sectional shaped stent can still provide the desired swirl inducing effect providing the centre line of the lumen is helical.

FIGS. 4 and 5 show an embodiment of a stent of the so-called helical spiral type. In this case the basic stent design consists of a wire 10 in a wave form, shown at 12, with that wave form extending in the manner of a coil from one end of the stent to the other. Longitudinally adjacent waves of the wave form 12 are joined by connecting elements 14. In the expanded condition the wavelength of the waves is, for most of the circumference of the stent, a distance D. In the region of the helical portion 6 this wavelength is reduced to less than D. The effect of the reduced wavelength is to cause the lumen of the fluid conduit in which the stent is expanded to adopt the desired configuration for promoting swirl flow in the lumen of the fluid conduit.

In the collapsed condition of the stent of FIGS. 4 and 5 the wavelength of the waves of the wave form 12 is reduced throughout the stent. During expansion the wavelength in the region of the helical portion 6 increases least. Extension in the circumferential direction is resisted by the helical portion 6. This could for example be achieved providing that the natural shape of the waves in the helical portion 6 is one having a smaller wavelength than D. This may be appropriate for example if the stent is made by being cut out from a metal sheet or tube.

Another way of achieving the reduced circumferential expansion in the region of the helical portion 6 would be to provide short bridges 16 between circumferentially adjacent portions of the wave in the helical portion 6. Such a bridge 16 is shown in FIG. 5. Further bridges would be provided at intervals along the helical portion.

FIG. 7 shows a stent of the closed cell type with "v" hinges between adjacent cells. In this case the helical portion 6 is provided by forming a helical line of cells 18 which are smaller than the other cells 20. When the stent is expanded, either by a balloon, or by the elastic or shape-memory properties of the material from which the stent is formed, the cells 20 expand to a predetermined size. The cells 18 expand to a smaller predetermined size and hence resist extension. As with the other stents, the result is that the lumen of the fluid conduit in which the stent is expanded adopts a configuration promoting swirl flow.

The various stents shown and described are provided with a single helical portion 6. However, other numbers of helical portions could be provided. Preferably the stents are non-rotationally symmetrical (rotational symmetry of order 1), as this can ensure that the centre line of the expanded stent follows a helical path.

Figure 14:
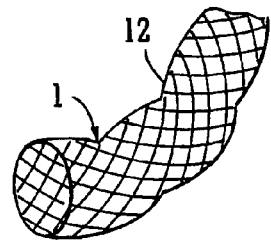
FIG. 14 is a perspective view of a stent.

FIG. 14 shows an internal stent 12 for use in a graft vessel or an intact vessel. The stent 12 is fabricated from a linked wire mesh and has a helical form along substantially the whole length of the stent. The material used is preferably a shape memory alloy to facilitate insertion of the stent.

Figure 15:
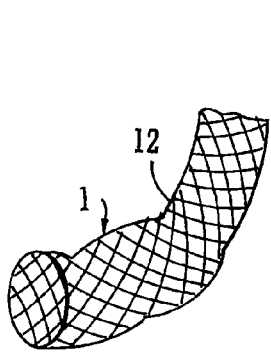
FIG. 15 is a perspective view of another stent.

FIG. 15 shows an alternative embodiment of an internal stent 12, in which the linked wire mesh has a helical tubing portion 1 only over a short region at one end thereof.

Figure 16:
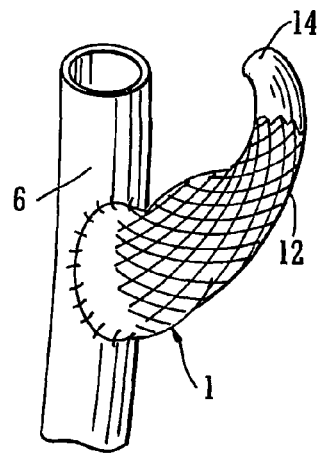
FIG. 16 is a perspective view of the stent of FIG. 15 internally supporting an arterial graft part.

FIG. 16 shows the stent 12 located in a graft 14 post insertion. The graft 14 surgically attached to an artery 6 has been shown transparent for purposes of illustration, to show the internally located, part helical wire mesh stent in-situ.

In the case of the internal stents of FIGS. 14, 15 and 16, in order to avoid the mesh itself forming a honeycomb of stagnant regions, a modification may involve providing the mesh with a smooth internal lining. Alternatively, an inner layer of the stent may be helically wound, without linkages, as described in WO 01/45593.

The helical form of the stents is arranged to promote swirl flow and thereby minimise flow instability and development of pathology.

The stents shown in FIGS. 14 and 15 are defined within an envelope with a curved longitudinal axis. They are generally arch shaped. Such an arch may curve in a single plane or may itself be non-planar, in which case the non-planarity should promote swirl flow in the same direction as the helix.

Figure 17:
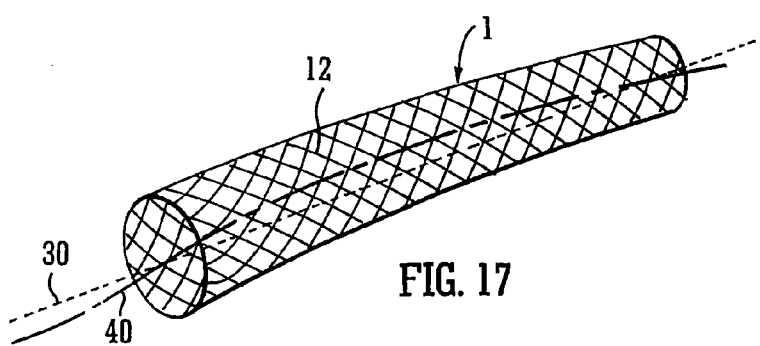
FIG. 17 is a perspective view of an internal arterial stent.

The stents need not be arch shaped; they may instead have a generally straight axis, as shown for example in FIG. 17. The stent of FIG. 17 has a straight central longitudinal axis 30, with a helical centre line 40 which undergoes about half of one turn. The low amplitude of the helix of the stent means that it is close to a cylindrical shape and can therefore be used in procedures where conventional stents would previously have been used. However, this is achieved without departing from a circular cross-sectional shape and without using helical ribs or other projecting formations. It is expected that the vessel into which the stent is inserted will be able to adopt the shape defined by the stent and therefore benefit from swirl flow. In other embodiments, the helical centre line may undergo more than half of one turn, and indeed more than one or more turns.

The stent of FIG. 17 may be useful as an arterial stent where there is thrombosis or stenosis of for example coronary arteries.

Figure 8:
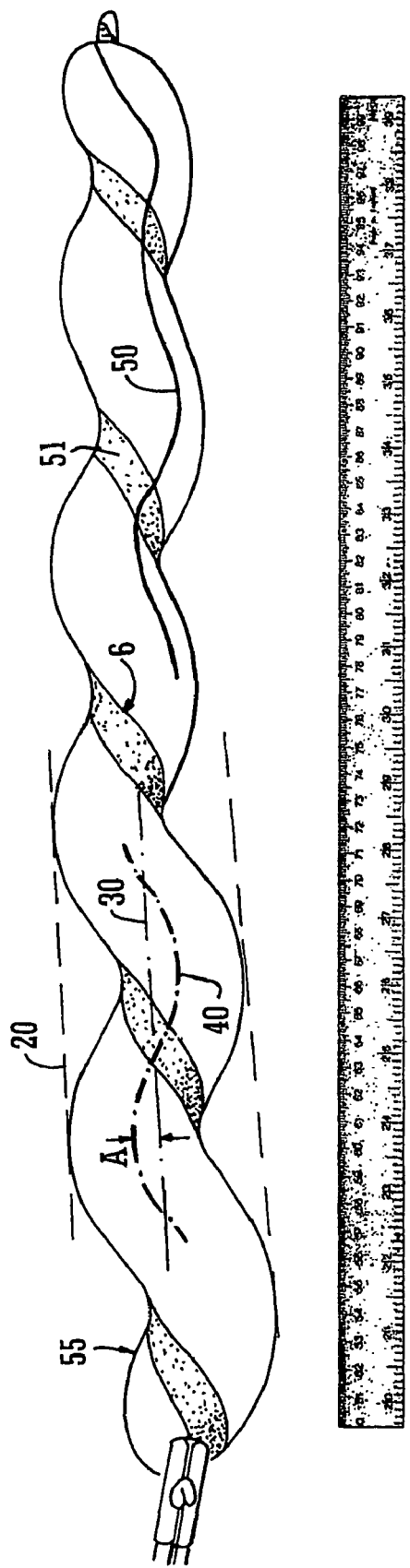
FIG. 8 is a view of an experimental balloon.

FIG. 8 shows the result of an experiment carried out on a toy balloon 55. The balloon was of the elongated type. It was supported, without being inflated, on a cylindrical rod and a plastic strip 51 cut from another balloon was glued onto the outside of the supported balloon to form a longitudinally and circumferentially extending helical strip 6. A straight line 50 was drawn along the balloon. After the glue had set, the balloon was inflated and the inflated balloon is shown in FIG. 8.

It will be seen that the inflated balloon 55 has a helical lumen. As with the stents, it has a helical centre line 40, which follows a helical path about a longitudinal axis 30. The longitudinal axis is at the centre of an imaginary cylindrical envelope 20 within which the balloon is contained. The amplitude A of the helix is shown in FIG. 8.

It will be noted that after inflation the straight line 50 adopts a wave shape which remains consistently along the same side of the balloon, so that the entire line 50 remains visible in the elevation view of FIG. 8. This indicates that the balloon has gone from the collapsed condition to the inflated condition without any significant twisting. There is no net twisting along the length of the balloon. A similar effect in an expanding stent in accordance with the preferred embodiments of the invention means that as the stent expands and engages the inside of a fluid conduit in which it is sited it does not impose excessive torsional loads on that conduit. This is beneficial in the case of the conduit being a blood vessel, for example, since torsion is resisted by the external tethering of the blood vessel.

Thus in the preferred embodiments the stents expand from the collapsed condition to the expanded condition without substantial twisting. The lack of twisting of the stent also enables it to have a plurality of turns without causing e.g. a blood vessel to twist during expansion, such twisting being undesirable because of the tethering of the blood vessel.

The balloon of FIG. 8 starts as a cylindrical membrane with a helical portion which is of greater (in this case double) wall thickness than the rest of the balloon. During inflation the thicker helical portion will tend to resist extension in all directions, including circumferential and longitudinal directions, thereby influencing the shape of the expanded balloon. Instead of adopting the normal cylindrical shape, the balloon forms a shape with a helical centre line 40.

FIG. 8 shows that the amplitude A achieved by the helical portion is much greater than would be achieved by simple rotation of a non-circular cross-section. The diameter of the envelope 20 is substantially greater than the diameter of the balloon. The same effect is obtained for an expanded stent outer wall or the wall of a balloon used in a balloon expandable stent.

Figure 9:
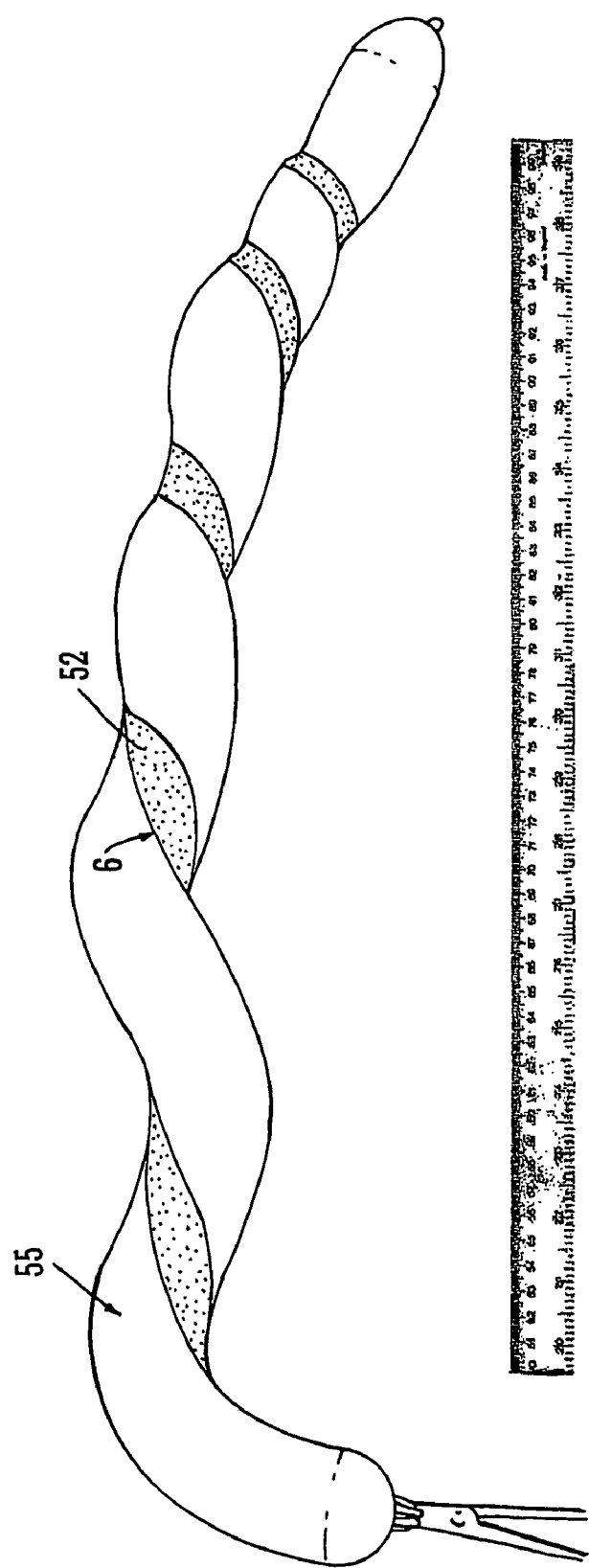
FIG. 9 is a view of another experimental balloon.

In another experiment, a plastic strip 52 was made with a tapered width, rather than with parallel side edges. It was found that the amplitude A of the helical centre line 40 was larger where the width of the strip was wider. This is shown in FIG. 9. A thinner strip tends to cause less deviation of the cross-sectional shape of the balloon from a circular shape.

The shape of the expanded experimental balloon membranes may be considered as analogous to that of an expanded stent outer wall or the wall of a balloon used in a balloon expandable stent. Considering therefore the inside of the helical balloon as a lumen or flow path, it will be appreciated that a helical lumen is obtained, giving the desirable flow properties discussed above, without the use of ribs, vanes or other flow guides protruding into the flow.

The experimental results thus show that by introducing a helical portion which resists extension during expansion of a stent, when expanded the stent will adopt a shape causing a fluid conduit which it supports to have a helical lumen, thereby promoting swirl flow. The effect observed in the balloons of FIGS. 8 and 9 may be obtained in a main stent body, either self-expanding or balloon expandable, and/or in a balloon which is used to expand a balloon expandable stent.

Figure 10:
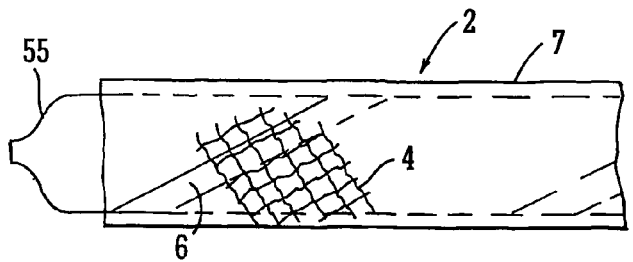
FIG. 10 is a side view of part of a balloon expandable stent, before expansion.

FIG. 10 shows a balloon expandable stent 2. A balloon 55 is provided with a helical strip 6. Upon inflation, the balloon causes the stent 2 to adopt the desired helical geometry, expanding to a shape as shown in the experimental balloon of FIG. 8. The stent is designed to deform plastically so that it holds to the shape supporting a conduit e.g. blood vessel so as to have a helical flow lumen.

It will be noted that in the preferred embodiments the stent does not rely on the use of thicker wires which themselves provide ribs or flow guides in an otherwise circular cross-section lumen. Rather, the shape of the lumen is modified by the resistance of the helical portion to extension.

Figure 11:
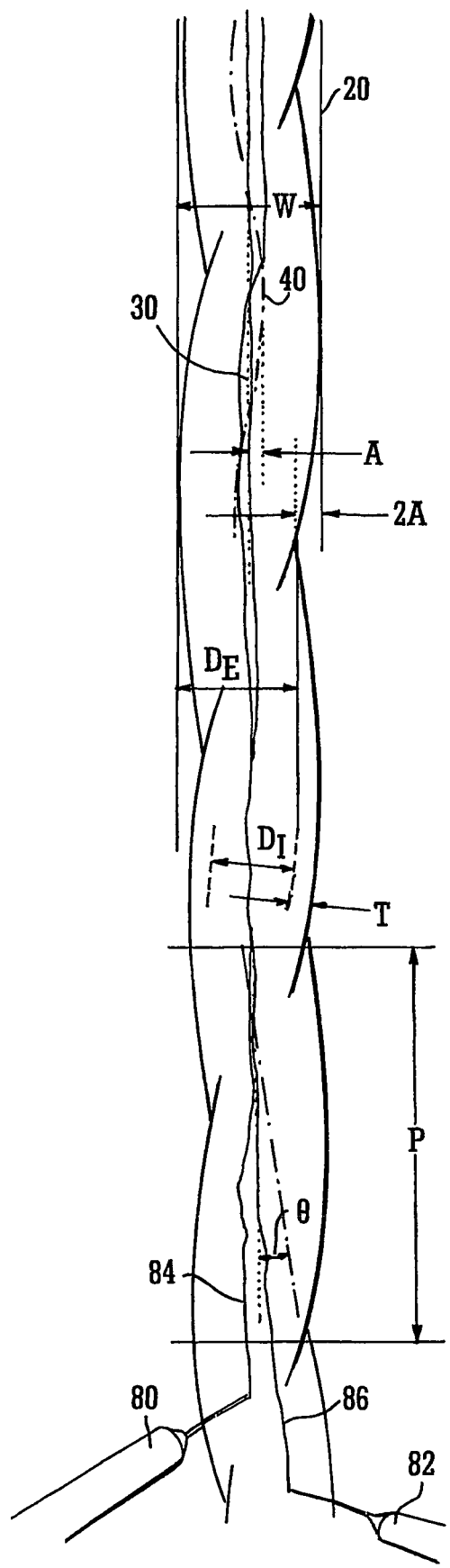
FIG. 11 is an elevation view of a tubing portion having a flow lumen in accordance with certain aspects of the invention.

The tubing portion 1 shown in FIG. 11 has a circular cross-section, an external diameter $D_E$, an internal diameter $D_I$ and a wall thickness T. The tubing is coiled into a helix of constant amplitude A (as measured from mean to extreme), constant pitch P, constant helix angle θ and a swept width W. The tubing portion 1 is contained in an imaginary envelope 20 which extends longitudinally and has a width equal to the swept width W of the helix. The envelope 20 may be regarded as having a central longitudinal axis 30, which may also be referred to as an axis of helical rotation. The illustrated tubing portion 1 has a straight axis 30, but it will be appreciated that in alternative designs the central axis may be curved. The tubing portion has a centre line 40 which follows a helical path about the central longitudinal axis 30.

It will be seen that the amplitude A is less than the tubing internal diameter $D_I$. By keeping the amplitude below this size, the space occupied by the tubing portion can be kept relatively small, whilst at the same time the helical configuration of the tubing portion promotes swirl flow of fluid along the tubing portion.

EXAMPLE 1

Figure 12:
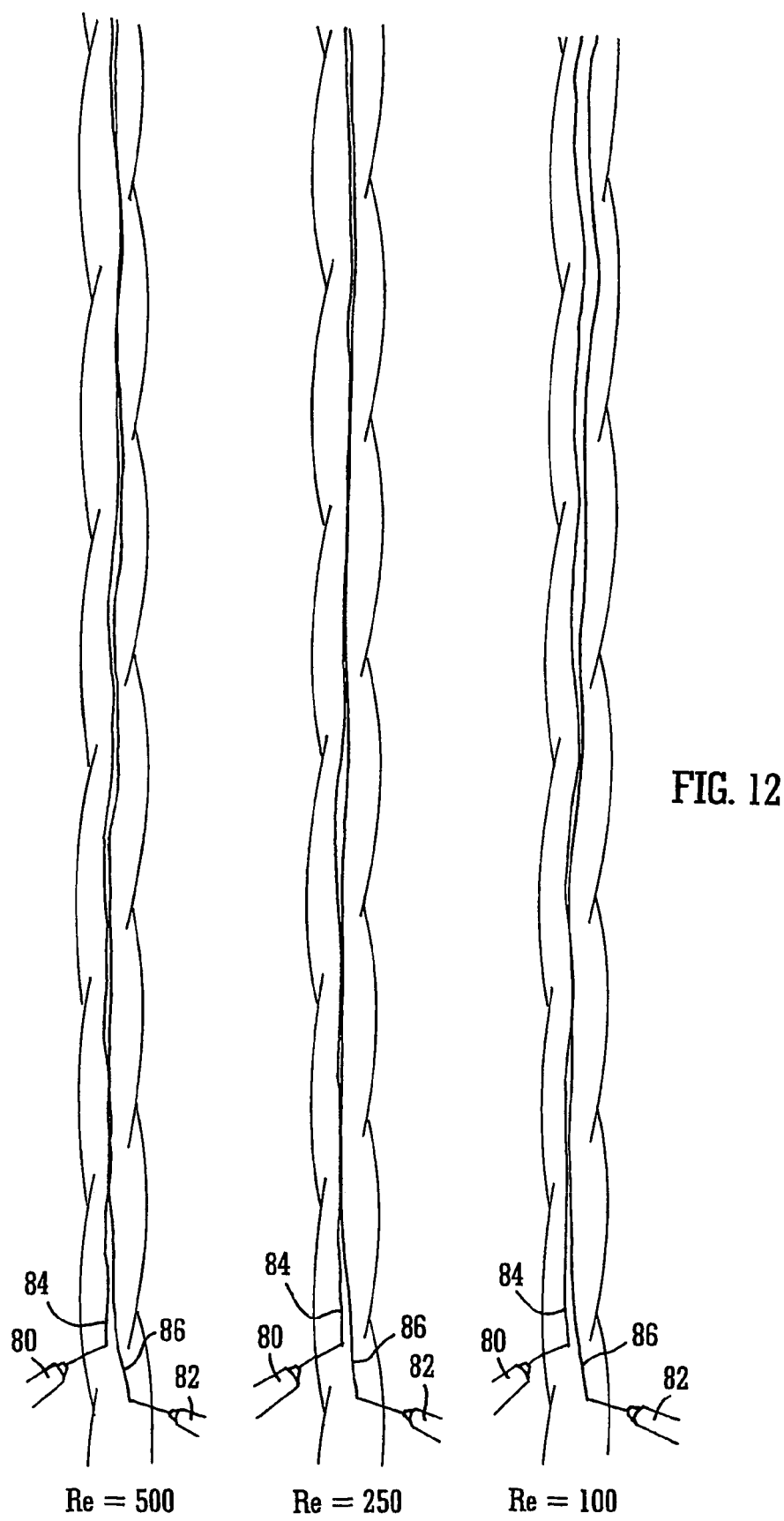
FIG. 12 shows elevation views of tubing portions used in experiments.

Experiments were carried out using polyvinyl chloride tubing with a circular cross-section. Referring to the parameters shown in FIG. 12 the tubing had an external diameter $D_E$ of 12 mm, an internal diameter $D_I$ of 8 mm and a wall thickness T of 2 mm. The tubing was coiled into a helix with a pitch P of 45 mm and a helix angle θ of 8°. The amplitude A was established by resting the tubing between two straight edges and measuring the space between the straight edges. The amplitude was determined by subtracting the external diameter $D_E$ from the swept width W:

$$2A = W - D_E$$

So:

$$A = \frac{W - D_E}{2}$$

In this example the swept width W was 14 mm, so:

$$A = \frac{W - D_E}{2} = \frac{14 - 12}{2} = 1 \text{mm}$$

As discussed earlier, "relative amplitude" $A_R$ is defined as:

$$A_R = \frac{A}{D_I}$$

In the case of this Example, therefore:

$$A_R = \frac{A}{D_I} = \frac{1}{8} = 0.125$$

Water was passed along the tube. In order to observe the flow characteristics, two needles 80 and 82 passing radially through the tube wall were used to inject visible dye into the flow. The injection sites were near to the central axis 30, i.e. at the "core" of the flow. One needle 80 injected red ink and the other needle 82 blue ink.

FIG. 11 shows the results of three experiments, at Reynolds numbers $R_E$ of 500, 250 and 100 respectively. It will be seen in all cases that the ink filaments 84 and 86 intertwine, indicating that in the core there is swirl flow, i.e. flow which is generally rotating.

EXAMPLE 2

Figure 13:
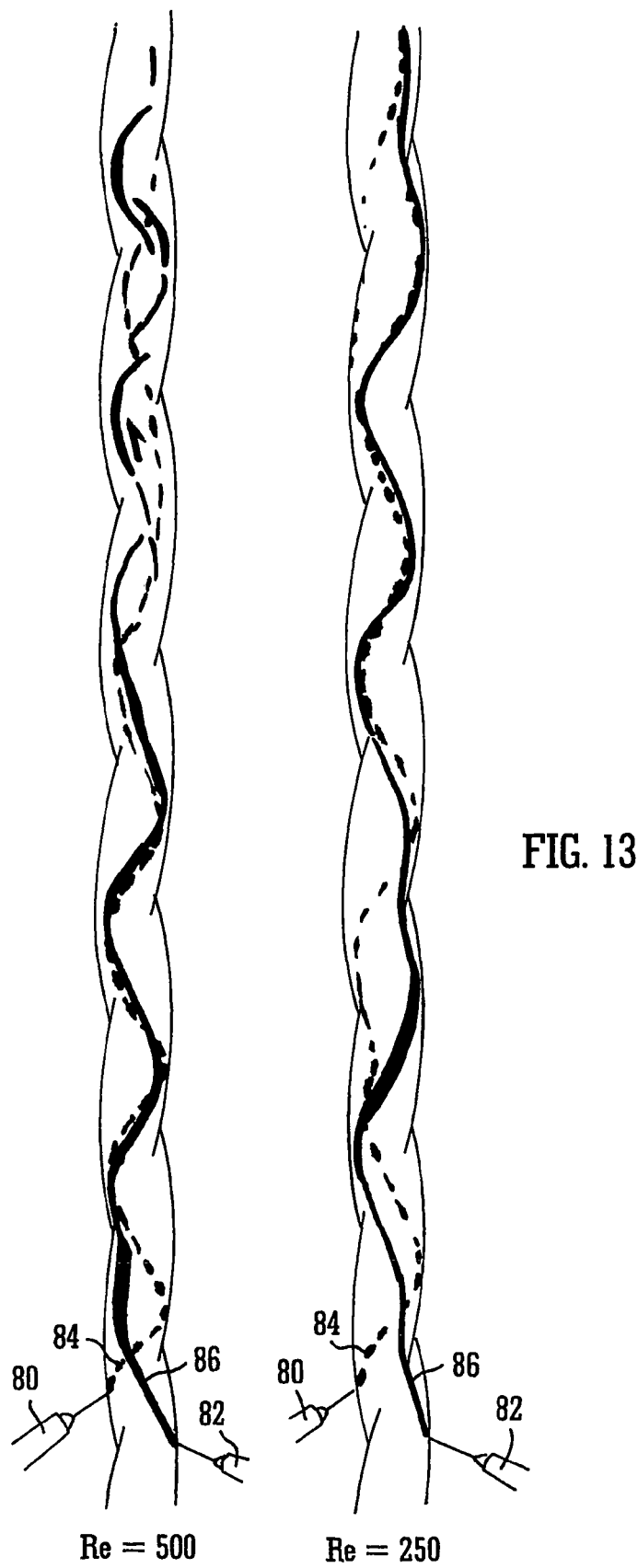
FIG. 13 shows elevation views of tubing portions used in further experiments.
Figure 18:
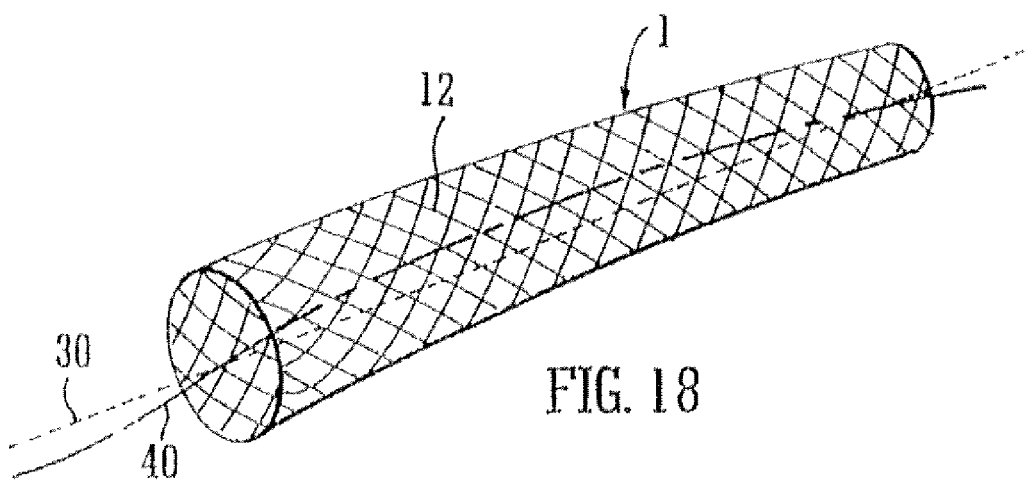

The parameters for this Example were the same as in Example 1, except that the needles 80 and 82 were arranged to release the ink filaments 84 and 86 near to the wall of the tubing. FIG. 13 shows the results of two experiments with near-wall ink release, with Reynolds numbers $R_E$ of 500 and 250 respectively. It will be seen that in both cases the ink filaments follow the helical tubing geometry, indicating near-wall swirl. Furthermore, mixing of the ink filaments with the water is promoted.

It will be appreciated that this invention, in its third and fourth aspects, is concerned with values of relative amplitude $A_R$ less than or equal to 0.5, i.e. small relative amplitudes. In a straight tubing portion both the amplitude A and the relative amplitude $A_R$ equal zero, as there is no helix. Therefore, with values of relative amplitude $A_R$ approaching zero, the ability of the tubing portion to induce swirl will reduce. The lowest workable value of relative amplitude $A_R$ for any given situation will depend on the speed of flow and the viscosity and density of the fluid (i.e. Reynolds number) and on the pitch (helix angle) and the particular use of the tubing portion.

Relative amplitudes of at least 0.05, 0.10, 0.15, 0.20, 0.25, 0.30, 0.35, 0.40 or 0.45 may be preferred.

The invention claimed is:

1. A stent for insertion in a fluid conduit of a human or animal body when the stent is in a collapsed condition and for expansion to an expanded condition, the stent comprising:
    an outer wall for engagement with the fluid conduit, the outer wall defining an internal diameter of the stent, wherein in the expanded condition the stent has a center line which follows a substantially helical path, so as to promote a swirl flow effect within the fluid conduit supported by the stent, and wherein the stent when expanded ex vivo has a helix angle less than or equal to 65° and a helical center line having an amplitude less than or equal to 0.7 of the internal diameter of the stent;
    wherein the stent, in the expanded condition, is substantially free of ribs which would project into a flow lumen of the conduit; and
    wherein the helix angle and/or amplitude of the helical center line varies along the length of the stent so as to introduce a swirl flow effect at an upstream end of the stent and to increase the swirl flow effect in a downstream direction.

2. A stent as claimed in claim 1, being a self-expanding stent.

3. A stent as claimed in claim 1, being a balloon expandable stent.

4. A stent as claimed in claim 1, wherein the amplitude of the helical centre line of the stent divided by the internal diameter of the stent is at least 0.05.

5. A stent as claimed in claim 1, wherein the helix angle is less than or equal to 15°.

6. A stent as claimed in claim 1, wherein the flow lumen of the conduit supported by the stent is of substantially circular cross-section.

7. A stent as claimed in claim 1, wherein the helical centre line of the conduit supported by the stent extends over just part of the overall length of the stent.

8. A stent as claimed in claim 1, wherein the helical centre line of the conduit supported by the stent extends over substantially the entire length of the stent.

9. A stent as claimed in claim 1, wherein the centre line of the stent follows a substantially helical path about an axis which is curved.

10. A stent as claimed in claim 1, further comprising a pharmaceutical coating.

11. A stent as claimed in claim 1 wherein the amplitude of the helical center line of the stent divided by the internal diameter of the stent is at least 0.1.

12. A stent as claimed in claim 1 wherein the stent undergoes at least one turn of the substantially helical path.

13. A stent as claimed in claim 1 wherein a helical portion of the stent has the same number of turns both when the stent is collapsed and when it is expanded.

14. A stent as claimed in claim 1, wherein the amplitude and the pitch of the helical center line vary along the length of the stent.

* * * * *